(12) United States Patent
Tabb et al.

(10) Patent No.: US 10,465,252 B2
(45) Date of Patent: Nov. 5, 2019

(54) BORDETELLA DETECTION ASSAY

(75) Inventors: Michelle M. Tabb, Santa Ana, CA (US); Ming-Chou Lee, Mission Viejo, CA (US); Lilly I. Kong, Covina, CA (US); Ning Lu, Pleasanton, CA (US); Michael Aye, Fountain Valley, CA (US); Fan Chen, Fullerton, CA (US); Jules Chen, Walnut, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 966 days.

(21) Appl. No.: 12/116,364

(22) Filed: May 7, 2008

(65) Prior Publication Data
US 2009/0197262 A1    Aug. 6, 2009

Related U.S. Application Data

(60) Provisional application No. 61/066,159, filed on Oct. 26, 2007.

(51) Int. Cl.
*C12Q 1/689* (2018.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,135,717 A | 8/1992 | Renzoni et al. | |
| 5,652,099 A | 7/1997 | Conrad | |
| 5,714,327 A | 2/1998 | Houthoff et al. | |
| 6,268,132 B1 | 7/2001 | Conrad | |
| 2003/0165866 A1 | 9/2003 | Cockerill et al. | |
| 2004/0265853 A1 | 12/2004 | Cockerill, III et al. | |
| 2006/0088865 A1* | 4/2006 | Adelson .................. | C12Q 1/705 435/6.16 |

FOREIGN PATENT DOCUMENTS

WO    WO 2002/061141    8/2002

OTHER PUBLICATIONS

GenBank Accession No. M28220 for Bordetella pertussis IS481, Aug. 4, 1993 [online], [retrieved on Nov. 7, 2010], retrieved from the Internet: <URL:www.ncbi.nlm.nih.gov/nuccore/341873>.*
Buck et al. Design strategies and performance of custom DNA sequencing primers. BioTechniques (1999) 27(3): 528-536.*
Van der Zee et al. Characterization of IS1001, an Insertion Sequence Element of Bordetella parapertussis. Journal of Bacteriology (1993) 175(1): 141-147.*
Lowe et al. A computer program for selection of oligonucleotide primers for polymerase chain reactions. Nucleic Acids Research (1990) 18(7): 1757-1761.*
BLAST search results of Bordetella parapertussis IS1001 (GenBank Accession No. X66858) run on Feb. 23, 2012. 3 pages.*
BLAST search results of Bordetella pertussis (GenBank Accession No. M28220) run on Feb. 23, 2012. 5 pages.*
Anton et al. International Journal of Systematic & Evolutionary Microbiology (2002) 52: 485-491.*
Valent et al. Genetics (1991) 127(1): 87-101.*
Schweitzer et al. Current Opinion in Biotechnology (2001) 12: 21-27.*
Ippolito et al. European Journal of Plant Pathology (2004) 110: 833-843.*
Sialer et al. Bulletin OEPP/EPPO Bulletin (2000) 40: 437-440.*
Van der Zee et al. Journal of Clinical Microbiology 1993; 31: 2134-2140 (Year: 1993).*
Fan et al. Clinical Infectious Diseases 1998; 26: 1397-1402 (Year: 1998).*
Campbell et al. Journal of Clinical Microbiology 1992; 30: 434-439 (Year: 1992).*
Contini et al. Interdisciplinary Perspectives on Infectious Diseases 2010; 2010: 273573 (Year: 2010).*
Makela et al. Journal of Clinical Microbiology 1998; 36: 539-542 (Year: 1998).*
International Search Report for PCT Patent Application No. PCT/US2002/079081, dated Feb. 26, 2009.
Antila et al., Bordetella holmesii DNA is not detected in nasopharyngeal swabs from Finnish and Dutch patients with suspected pertussis, Journal of Medical Microbiology, 55, p. 1043-1051, (2006).
Backman el al., Nested PCR optimized for detection of Bordetella pertussis in clinical nasopharyngeal samples, Journal of Clinical Microbiology, vol. 32, No. 10, p. 2544-2548, (1994).
Chan et al., The use of TaqMan PCR assay for detection of bordetella pertussis infection from clinical specimens, Arch. Pathol. Lab. Med., 126:173-176, (2002).
Dragsted et al., Comparison of culture and PCR for detection of Bordetella pertussis and Bordetella parapertussis under routine laboratory conditions, Journal of Medical Microbiology, 53, p. 749-754, (2004).
Elomaa et al., Strain variation among Bordetella pertussis isolates in Finland, where the whole-cell pertussis vaccine has been used for 50 years, Journal of Clinical Microbiology, 43:3681-3687, (2005).
Farrell et al., Nested duplex PCR to detect Bordetella pertussis and Bordetella parapertussis and its application in diagnosis of pertussis in nonmetropolitan Southeast Queensland, Australia, Journal of Clinical Microbiology, vol. 37, No. 3, p. 606-610, (1999).
Farrell et al., Rapid-cycle PCR method to detect Bordetella pertussis that fulfills all consensus recommendations for use of PCR in diagnosis of Pertussis, Journal of Clinical Microbiology, vol. 38, No. 12, p. 4499-4502, (2000).
Hafner, et al., Isothermal Amplification and Multimerization, Biotechniques Apr;30(4):852-6, 858, 860 (2001).

(Continued)

Primary Examiner — Angela M. Bertagna
(74) Attorney, Agent, or Firm — Foley & Lardner LLP

(57) ABSTRACT

Disclosed herein are methods and compositions for detecting *Bordetella pertussis* and *Bordetella parapertussis* by detecting the presence of the IS481 and IS1001 genomic insertion sequences, respectively.

13 Claims, 2 Drawing Sheets

Specification includes a Sequence Listing.

(56) References Cited

OTHER PUBLICATIONS

He et al., Comparison of polymerase chain reaction with culture and enzyme immunoassay for diagnosis of pertussis, Journal of Clinical Microbiology, 31:642-645, (1993).

Heid, et al., Real time quantitative PCR, Genome Res 6: 986-994 (1996).

Hoppe, Update on respiratory infection caused by Bordetella parapertussis, Pediatr. Infect. Dis. J., 18:375-381, (1999).

Iwata et al., Mixed outbreak of Bordetella pertussis and Bordetella parapertussis in an apartment house, Dev. Biol. Stand., 73:333-341, (1991).

Jameson et al., Fluorescent Nucleotide Analogs: Synthesis and Applications, Meth. Enzymol. 278:363-390 (1997).

Kerr et al., Bordetella pertussis infection: Pathogenesis, diagnosis, management, and the role of protective immunity, Eur. J. Clin, Microbiol. Infect. Dis., 19:77-78, (2000).

Knorr et al., Evaluation of real-time PCR for diagnosis of Bordetella pertussis infection, BMC Infectious Diseases, 6:62, (2006).

Koidl et al., Detection and differentiation of *Bordetella* spp. by real-time PCR, Journal of Clinical Microbiology, vol. 45, No. 2, p. 347-350, (2007).

Kosters et al., Evaluation of a real-time PCR assay for detection of Bordetella pertussis and B. parapertussis in clinical samples, J. Med. Microbiol., 50:436-440, (2001).

Kosters et al., Real-time lightcycler PCR for detection and discrimination of Bordetella pertussis and Bordetella parapertussis, Journal of Clinical Microbiology, 40:1719-1722, (2002).

Lind-Brandberg et al., Evaluation of PCR for diagnosis of Bordetella pertussis and Bordetella parapertussis infections, Journal of Clinical Microbiology, vol. 36, No. 3, p. 679-683, (1998).

Linneman et al., Bordetella parapertussis, Recent experience and a review of the literature, Am. J. Dis. Child., 131:560-563, (1977).

Loeffelholz et al., Comparison of PCR, culture, and direct fluorescent-antibody testing for detection of bordetella pertussis, Journal of Clinical Microbiology, 37:9, p. 2872-2876, (1999).

Maniatis et al., DNA Transfection by Electroporation, Nucleic Molecular Cloning, A Laboratory Manual, 2d, Cold Spring Harbor Laboratory Press, p. 16.54 (1989).

Mansfield et al., Nucleic acid detection using non-radioactive labeling methods, Mol. Cell. Probes 9:145-156 (1995).

Mattoo et al., Molecular Pathogenesis, Epidemiology, and Clinical Manifestations of Respiratory Infections Due to *Bordetella pertussis* and Other *Bordetella* Subspecies, Clin. Microbiol. Rev., 18: 326-382 (2005).

Menard et al., Development of a real-time PCR for the identification of Bordetella pertussis and Bordetella parapertussis, Clinical MicroBiology and Infection, vol. 13, No. 4, (2007).

Mertsola, Mixed outbreak of Bordetella pertussis and Bordetella parapertussis infection in Finland, Eur. J. Clin. Microbiol., 4:123-128, (1985).

Nelson et al., Detection of Bordetella pertussis in clinical specimens by PCR and a microliter plate-based DNA hybridization assay, Journal of Clinical Microbiology, 35:117-120, (1997).

Prodesse Inc., ProPertussis Real Time Assay, for detection of Bordetella pertussis, Prodesse, rev. 1.2, P1467E, Aug. 2006.

Reischl et al., Real-time PCR assay targeting 1S481 of Bordetella pertussis and molecular basis for detecting Bordetella holmesii, Journal of Clinical Microbiology, p. 1963-1966, (2001).

Saiki, R.K., "Amplification of Genomic DNA" in PCR Protocols, Innis et al., Eds., Academic Press, San Diego, CA pp. 13-20 (1990).

Sloan et al., Multiplex lightcycler PCR assay for detection and differentiation of Bordetella pertussis and Bordetella parapertussis in nasopharyngeal specimens, Journal of Clinical Microbiology, vol. 40, No. 1, p. 96-100, (2002).

Templeton et al., Evaluation of real-time PCR for detection of and discrimination between Bordetella pertussis, Bordetella parapertussis, and Bordetella holmesii for Clinical Diagnosis, Journal of Clinical Microbiology, p. 4121-4126, (2003).

Tyagi et al., Multicolor molecular beacons for allele discrimination, Nature Biotechnology 16:49-53 (1998).

Van Der Zee et al., the differentiation of Bordetella parapertussis and Bordetella bronchiseptica from humans and animals as determined by DNA polymorphism mediated by two different insertion sequence elements suggests their phylogenetic relationship, International Journal of Systematic Bacteriology, vol. 46, No. 3, p. 640-647, (1996).

Van Der Zee et al., Polymerase chain reaction assay for Pertussis: Simultaneous detection and discrimination of Bordetella pertussis and Bordetella parapertussis, Journal of Clinical Microbiology, vol. 31, No. 8, p. 2134-2140, (1993).

Wadowsky et al., Multiplex PCR-based assay for detection of Bordetella pertussis in nasopharyngeal swab specimens, Journal of Clinical Microbiology, 34:2645-2649, (1996).

Wharam et al., Specific detection of DNA and RNA targets using a novel isothermal nucleic acid amplification assay based on the formation of a three-way junction structure, Nucleic Acids Res. Jun. 1;29(11):E54-E54 (2001).

Whitcombe et al., Detection of PCR products using self-probing amplicons and fluorescence, Nature Biotech 17:804-807 (1999).

Zhu et al. Directly labeled DNA probes using fluorescent nucleotides with different ength linkers, Nucl. Acids Res. 22:3418-3422 (1994).

He et al., Primers are Decisive for Sensitivity of PCR, Biotechniques, 17:82-87 (1994).

International Search Report and Written Opinion dated Feb. 26, 2009 in application PCT/US2008/079081.

Cloud et al, Evaluation of a lightcycler(R) PCR assay to simultaneously detect bordetella pertussis and B. parapertussis, Abstracts of the General Meeting of the American Society for Microbiology, (2002), 102:147.

Database Geneseq [online] Oct. 17, 2002, Bordetella parapertussis insertion sequence IS1001 SEQ ID No. 10, retrieved from EBI accession No. GSN:ABQ74447.

McLafferty et al, Nucleotide sequence and characterization of a repetitive DNA element from the genome of bordetella pertussis with characteristics of an insertion sequence, J Gen Microbiology, (1988), 134(8):2297-2306.

* cited by examiner

FIGURE 1

```
   1 gcgaggccgg ctatctgtga agattcaata ggttgtatgc atggttcatc cgaaccggat
  61 ttgagaaact ggaaatcgcc gacccccag ttcactcaag gagcccggcc ggatgaacac
 121 ccataagcat gcccgattga ccttcctacg tcgactcgaa atggtccagc aattgatcgc
 181 ccatcaagtt tgtgtgcctg aagcggcccg cgcctatggg gtcaccgcgc cgactgtgcg
 241 caaatggctg ggccgcttcc tggctcaggg ccaggcgggc ttggccgatg cgtcctcgcg
 301 cccgacggtc tcgccccgag cgattgcgcc ggccaaggcg ctggctatcg tggagctgcg
 361 ccgcaagcgg ctgacccaag cgcgcatcgc ccaggcgctg ggcgtgtcag ccagcaccgt
 421 cagccgcgtc ctggcccgcg ccggtctgtc gcacctggcc gacctggagc cggccgagcc
 481 ggtggtgcgc tacgagcatc aggcccccgg cgatctgctg cacatcgaca tcaagaagct
 541 gggacgtatc cagcgccctg gccaccgggt cacgggcaac cgacgcgata ccgttgaggg
 601 ggccggctgg gacttcgtct tcgtggccat cgatgaccac gcccgcgtgg ccttcaccga
 661 catccccccc gacgagcgct tccccagcgc cgtccagttc ctcaaggacg cagtggccta
 721 ctaccagcgc ctgggcgtga ccatccagcg cttgctcacc gacaatggct cggcctttcg
 781 cagccgcgcc ttcgccgcgc tgtgccatga gctgggcatc aagcaccgct ttacccgacc
 841 ttaccgccca cagaccaatg gcaaggccga acgcttcatc cagtcggcct tgcgtgagtg
 901 ggcttacgct cacacctacc agaactccca acaccgagcc gatgccatga aatcctggct
 961 acaccactac aactggcatc gacccacca aggcatcggg cgcgctgtac ccatctccag
1021 actcaacctg gacgaataca acctattgac agttcacagc tatccggacc ggc
```

(SEQ ID NO: 1)

FIGURE 2

```
   1 ggttcatcgc gcaataacgt ggaggggttt ggcaattttc gtattcttga cggcaggtat
  61 ttgacatcag gagtgcaggg agatgctgga tcgcaagttg atggagtcgc tgggaggctg
 121 gcagggctat ggcgtcgaac gcgtggaatg gcccgaagac ccagggcgca cgctgtcgat
 181 ctatttgaag ccaacggcca aggtgatgct gtgcgagcag tgcggcgcgc ggtgtcgcca
 241 ggtgcatgag accacggttc gacgggtgcg agatctgccg atattcgagt atcgggtcgt
 301 tctgcacgtg ccgcgccgac gcttgtggtg tgagcaatgc ggcggcccgc gcctggagcg
 361 gcttgcctgg ctgggcgat atcaacgggt gacggatcgg ctggcgcagg cctgcagcca
 421 attgctgcaa tcgagcaacg tgcaggcggt ggcgaggttc ttcgaactgg gttggcatac
 481 cgtcaagacg ctggacaagg ctcggctgcg tgcgtcggtg cgcgaaccgg attggtccaa
 541 gatcgagtat ttggcgatgg acgagtttgc cctgcacaaa gggcatcgct acgcgacagt
 601 ggtggtcgat ccgatcggca ggcaggtgct gtggattggc ccaggacgct cacgcgagac
 661 ggcccgggcg ttcttcgaac aattgccgcc tggggccgcc caacgcatca aggccgttgc
 721 catcgacatg accaccgcct acgagttgga gatccaggcc cacagcccac aggcggagat
 781 cgtctatgac ttgttccatg tcgtggccaa gtatggacga gaggtcattg atcgggtgcg
 841 cgtggatcag gccaatcaac tacgccagga tcgtcccgca cgcaggatca tcaaatcgag
 901 tcgctggctg ctgctgcgca accgtgacaa cctggatcgg cagcaggccg tccggctcga
 961 cgaattgctg caagccaacc agccgctgct gacggtctat gtcctgcgtg acgaactcaa
1021 acggctctgg ttctaccaaa gacctgcctg ggcaagacaa gcctggaacc actggtacga
1081 gcaggccgag caaagcggaa tagccgcctt gaacaccttc gctcagcgct tgaaaggcta
1141 tctgcacggc atcctggcca gatgccgaca tccccctgaac accagcattg tcgagggcat
1201 caacaacact atcaaggtca tcaagcggcg cgcttacggc taccgcgacc aggaatactt
1261 cttcctcaaa atccgtgccg ccttccccgg caatgcgcga tgaacc
```

(SEQ ID NO: 7)

BORDETELLA DETECTION ASSAY

CROSS-REFERENCE TO RELATED APPLICATIONS

This application claims benefit of U.S. Provisional Application 61/066,159, filed Oct. 26, 2007, which is incorporated in its entirely herein by reference thereto.

FIELD OF INVENTION

This invention relates to the field of pathogen detection.

BACKGROUND OF INVENTION

The following discussion of the background of the invention is merely provided to aid the reader in understanding the invention and is not admitted to describe or constitute prior art to the present invention.

Whooping cough is a highly contagious disease of the respiratory system. Symptoms of whooping cough include episodes of violent cough followed by an inspiratory whoop and sometimes vomiting. In extreme cases these symptoms lead to hypoxia, permanent brain damage or even death. The majority of cases (80-98%) are caused by the small gram-negative bacteria *Bordetella pertussis*; however, a significant minority of cases (2-20%) are caused by *Bordetella parapertussis*. (Mattoo et al., Clin. Microbiol. Rev., 18: 326-382, 2005). Symptoms of whooping cough caused by *B. parapertussis* are typically milder than those caused by *B. pertussis*; however, a differential diagnosis is difficult based on clinical symptomology alone. Very rarely are pertussis-like symptoms caused by infection with *B. bronchiseptica* or *B. holmesii*.

Diagnosing whooping cough in its early stages can be difficult because the signs and symptoms resemble those of other common respiratory illnesses, such as a cold, the flu, or bronchitis. Traditionally, bacterial cultures have been used to definitively diagnose whooping cough. Mucus is obtained from the nose and/or throat of the patient and sent to a medical lab for culturing. Although positive results are regarded as conclusive, *Bordetella* cultures typically require 5 to 7 days to obtain a diagnosis. *Bordetella* sp. bacterial cultures are also prone to false negative results because of the fastidious nature of the bacteria.

Antibody assays, including FLISA, are also used to diagnose *Bordetella* sp. by detecting characteristic bacterial antigens. Most commonly, detection of the pertussis toxin protein is used as an indicium of *Bordetella* infection. Although these antibody-based assays have good sensitivity and specificity, they typically require a sample of patient blood, instead of a non-invasively obtained mucus sample, and further require the infection to be in the early and/or convalescent stage. These assays are therefore prone to false negative results if the patient sample is not obtained at the proper time in the disease process.

Other methods for detecting *Bordetella* infection include direct fluorescent antibody (DFA) testing and various PCR-based methods. DFA testing has the advantage of being able to detect *Bordetella* using non-invasively obtained mucus samples, but suffers from a lack of sensitivity. PCR-based assays are becoming more widely used.

SUMMARY OF THE INVENTION

The present invention provides compositions and methods for determining the presence or absence of *Bordetella pertussis* and/or *Bordetella parapertussis* in a biological sample. The invention may also be used alone, or in combination with clinical symptoms or other indicators, for diagnosing an individual as having whooping cough. Specifically, the present invention enables the detection of pathogenic bacteria (*Bordetella* spp.) known to cause whooping cough by detecting the presence of bacterial nucleic acids in the sample. The detection methodology is based on the discovery of particular target sequences within the bacterial genomes which are useful indicators of bacterial infection.

Accordingly, in one aspect, the invention provides a method for determining the presence or absence of *Bordetella pertussis* and/or *Bordetella parapertussis* in a biological sample, by: detecting the presence or absence of:
  (a) an IS481 target nucleic acid having at least 14 contiguous nucleotides that are at least 95% identical to SEQ ID NO: 2 or a complement thereof, and
  (b) an IS1001 target nucleic acid having at least 14 contiguous nucleotides that are at least 95% identical to SEQ ID NO: 8 or a complement thereof,
wherein the presence of said IS481 target nucleic acid identifies the presence of *B. pertussis*, and the presence of said IS1001 target nucleic acid identifies the presence of *B. parapertussis*.

In some embodiments, one or both of the IS481 target nucleic acid and the IS1001 target nucleic acid are amplified (e.g. by PCR).

In another embodiment, the method includes the steps of:
  (a) providing a first primer pair suitable for amplifying IS481 target nucleic acid or a fragment thereof, and providing a second primer pair suitable for amplifying IS1001 target nucleic acid or a fragment thereof,
  (b) performing a multiplex primer extension reaction comprising the primer pairs of step (a) under conditions suitable to produce a first reaction product when IS481 target nucleic acid is present in the sample, and a second reaction product when IS1001 target nucleic acid is present in the sample; and
  (c) determining the presence or absence of *Bordetella pertussis* by detecting the presence or absence of a first reaction product having at least 14 contiguous nucleotides that are at least 95% identical to the nucleotide sequence of SEQ ID NO: 2 or a complement thereof, and/or determining the presence or absence of *Bordetella parapertussis* by detecting the presence or absence of a second reaction product having at least 14 contiguous nucleotides that are at least 95% identical to the nucleotide sequence of SEQ ID NO: 8 or a complement thereof.

In another aspect, the invention also provides a method for determining the presence or absence of *Bordetella pertussis* in a biological sample by detecting the presence or absence of an IS481 target nucleic acid having at least 14 contiguous nucleotides of SEQ ID NO 2, or a complement thereof.

In one embodiment, the method for detecting *B. pertussis* includes the steps of:
  (a) providing a primer pair suitable for amplifying an IS481 target nucleic acid or a fragment thereof;
  (b) performing a primer extension reaction comprising the primer pair of step (a) under conditions suitable to produce a reaction product when IS 481 target nucleic acid is present in said sample; and
  (c) determining the presence or absence of *Bordetella pertussis* by detecting the presence or absence of a reaction product having at least 14 contiguous nucleotides that are at least 95% identical to the nucleotide sequence of SEQ ID NO: 2 or a complement thereof.

In another aspect, the invention also provides a method for determining the presence or absence of *Bordetella parapertussis* in a biological sample by detecting the presence or absence of an IS1001 target nucleic acid having at least 14 contiguous nucleotides of SEQ ID NO 8, or a complement thereof.

In one embodiment, the method for detecting *B. parapertussis* includes the steps of:
(a) providing a primer pair suitable for amplifying an IS1001 target nucleic acid or a fragment thereof;
(b) performing a primer extension reaction comprising the primer pair of step (a) under conditions suitable to produce a reaction product when IS1001 target nucleic acid is present in said sample; and
(c) determining the presence of *Bordetella parapertussis* by detecting the presence or absence of a reaction product having at least 14 contiguous nucleotides that are at least 95% identical to the nucleotide sequence of SEQ ID NO: 8 or a complement thereof.

In preferred embodiments of all aspects of this invention, the IS481 reaction product contains at least 20, 25, 30, 35, 40, 45, 50, 75, 100, 125, or 140 contiguous nucleic acids that are at least 95% (e.g., at least 99% or 100%) identical to SEQ ID NO: 2, or complements thereof. In other preferred embodiments, the IS481 reaction product is at least 95% (e.g., at least 99% or 100%) identical to at least 15, 20, 25, 30, 35, 40, 45, 50, 75, or 85 contiguous nucleic acids of SEQ ID NO: 3, or complements thereof. In other preferred embodiments, the IS481 reaction product is less than about 175, 150, 125, 100, or 75 nucleic acids in length.

In other preferred embodiments, at least one of the IS481 primers (i.e., primers suitable for amplifying IS481 or a fragment thereof) comprises a nucleic acid having the sequence of SEQ ID NO: 4 or 5, or a complement thereof. In one embodiment, the IS481 target nucleic acid is detected using an oligonucleotide probe. The oligonucleotide probe preferably has the sequence of SEQ ID NO: 6 or 27, or complements thereof and is detectably labeled. In other preferred embodiments, the detectable label is a fluorescent label.

In preferred embodiments of all aspects of this invention, the IS1001 reaction product contains at least 20, 25, 30, 35, 40, 45, 50, 75, 100, 125, 140, 160, or 180 contiguous nucleic acids that are at least 95% (e.g., at least 99% or 100%) identical to SEQ ID NO: 8, or complements thereof. In other preferred embodiments, the IS1001 reaction product is at least 95% (e.g., at least 99% or 100%) identical to at least 15, 20, 25, 30, 35, 40, 45, 50, or 70 contiguous nucleic acids of SEQ ID NO: 9, or complements thereof. In other preferred embodiments, the IS1001 target nucleic acid is less than about 175, 150, 125, 100, or 75 nucleic acids in length.

In other preferred embodiments, at least one of the IS1001 primers (i.e., primers suitable for amplifying IS1001 or a fragment thereof) comprises a nucleic acid having the sequence of SEQ ID NO: 10 or 11, or a complement thereof. In one embodiment, the IS1001 reaction product is detected using an oligonucleotide probe. The oligonucleotide probe preferably has the sequence of SEQ ID NO: 12, or a complement thereof and is detectably labeled. In other preferred embodiments, the detectable label is a fluorescent label.

In other preferred embodiments of any of the foregoing methods, the method further comprises real-time PCR. In other embodiments, at least one of the primers are Scorpion primers. Suitable IS481 Scorpion primers include, for example, a nucleic acid primer comprising the sequence of SEQ ID NOS: 13, 29, and 30 or SEQ ID NOS: 28 and 30, or complements thereof. Suitable IS1001 Scorpion primers include, for example, a nucleic acid primer comprising the sequence of SEQ ID NOS: 14 and 31, or a complement thereof.

In another aspect, the invention provides isolated nucleic acids encoding an IS481 target nucleic acid. The IS481 target nucleic acid is substantially identical to at least 20 (e.g., at least 25, 30, 35, 40, 45, 50, 75, 100, 125, or 140) contiguous nucleotides of SEQ ID NO: 2, or a complement thereof and is less than 1000 nucleotides (e.g., less than 750, 500, 250, 200, 175, 150, 125, 100, or 75 nucleotides) in length. In one embodiment, the IS481 target nucleic acid contains a nucleotide sequence that is substantially identical to at least 20 contiguous nucleotides of SEQ ID NO: 3.

In another aspect, the invention provides isolated nucleic acids encoding an IS1001 target nucleic acid. The IS1001 target nucleic acid is substantially identical to at least 20 (e.g., at least 25, 30, 35, 40, 45, 50, 75, 100, 125, 150, or 175) contiguous nucleotides of SEQ ID NO: 8, or a complement thereof, and is less than 1000 nucleotides (e.g., less than 750, 500, 250, 200, 175, 150, 125, 100, or 75 nucleotides) in length. In one embodiment, the IS1001 target nucleic acid contains a nucleotide sequence that is substantially identical to at least 20 contiguous nucleotides of SEQ ID NO: 9.

In another aspect, the invention provides oligonucleotide primers and probes suitable for amplifying and/or detecting an IS481 target nucleic acid or an IS1001 target nucleic acid. The IS481 primers and probes of the invention are 10-50 (e.g., 12, 14, 16, 18, 20, 22, 25, 30, 35, 40, or 45) nucleotides in length and are substantially identical, preferably 100% identical) to the corresponding nucleotide sequence of SEQ ID NO: 2. The IS1001 primers and probes of the invention are 10-50 (e.g., 12, 14, 16, 18, 20, 22, 25, 30, 35, 40, or 45) nucleotides in length and are substantially identical, preferably 100% identical) to the corresponding nucleotide sequence of SEQ ID NO: 8. In preferred embodiments, the IS481 primers and probes have a nucleotide sequence of SEQ ID NOs: 4-6 or 27. In other preferred embodiments, the IS1001 primers and probes have a nucleotide sequence of SEQ ID NOs: 10-12.

In another aspect, the invention provides Scorpion primers for amplifying and detecting an IS481 target nucleic acid an IS1001 target nucleic acid, wherein the Scorpion primer comprises a oligonucleotide probe sequence and an oligonucleotide primer sequence each of which individually conform to the requirements of an oligonucleotide primer and probe, respectively. In preferred embodiments, the IS481 Scorpion primer has the nucleotide sequence of SEQ ID NOS: 13, 29, and 30. In other preferred embodiments, the IS1001 Scorpion primer has the nucleotide sequence of SEQ ID NOS: 14 and 31.

In another aspect, the invention provides a kit containing:
(a) a first primer pair that specifically hybridizes to a nucleic acid having the sequence of SEQ ID NO: 2 or a complement thereof and a first probe capable of specifically hybridizing to a nucleic acid having the sequence of SEQ ID NO: 2 or a complement thereof, and
(b) a second primer that specifically hybridizes to the sequence of SEQ ID NO: 8 or a complement thereof, and a second probe capable of specifically hybridizing to a nucleic acid having the sequence of SEQ ID NO: 8, or a complement thereof.

In preferred embodiments, the first primer pair and/or the first probe are capable of specifically hybridizing to a nucleic acid having the sequence of SEQ ID NO: 3, or a complement thereof. Preferred members of the first primer pair have the sequences of SEQ ID NOs: 4-5, or complements thereof, and a preferred first probe has the sequence of SEQ ID NO: 6 or 27, or complements thereof.

In other preferred embodiments, the second primer pair and/or the second probe are capable of specifically hybridizing to a nucleic acid having the sequence of SEQ ID NO: 9, or a complement thereof. Preferred members of the second primer pair have the sequences of SEQ ID NOs: 10-11, or complements thereof, and a preferred second probe has the sequence of SEQ ID NO: 12.

Preferably, the probes further comprise a detectable label (e.g., a fluorescent label).

BRIEF DESCRIPTION OF THE FIGURES

FIG. 1 is the nucleotide sequence of the *B. pertussis* IS481 insertion sequence provided at GenBank Accession No. M28220 (SEQ ID NO: 1).

FIG. 2 is the nucleotide sequence of the *B. parapertussis* IS1001 insertion sequence provided at GenBank Accession No. X66858 (SEQ ID NO: 7).

DETAILED DESCRIPTION OF INVENTION

The present invention provides methods, compositions, and kits suitable for identifying *Bordetella pertussis* and/or *Bordetella parapertussis*, the pathogens most commonly associated with whooping cough. The invention is based on the real-time PCR detection of the insertion sequence IS481 of *B. pertussis* and/or the insertion sequence IS1001 of *B. parapertussis* in a biological sample obtained from an individual. These insertion sequences are advantageously used for PCR-based diagnostic assays because they have a relatively high genomic copy number. The *B. pertussis* genome typically contains about 100-200 copies of the IS481 sequence. And, the *B. parapertussis* genome typically contains about 20 copies of the IS1001 sequence.

As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

As used herein, "about" means plus or minus 10%.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplicon" or "amplification product." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam, et al., Nucleic Acids Res. 2001 Jun. 1; 29(11):E54-E54; Hafner, et al., Biotechniques 2001 April; 30(4):852-6, 858, 860; Zhong, et al., Biotechniques 2001 April; 30(4):852-6, 858, 860.

The term "complement" "complementary" or "complementarity" as used herein with reference to polynucleotides (i.e., a sequence of nucleotides such as an oligonucleotide or a target nucleic acid) refers to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA. The term "substantially complementary" as used herein means that two sequences specifically hybridize (defined below). The skilled artisan will understand that substantially complementary sequences need not hybridize along their entire length.

As used herein, the term "detecting" used in context of detecting a signal from a detectable label to indicate the presence of a target nucleic acid in the sample does not require the method to provide 100% sensitivity and/or 100% specificity. As is well known, "sensitivity" is the probability that a test is positive, given that the person has a target nucleic acid sequence, while "specificity" is the probability that a test is negative, given that the person does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

A "fragment" in the context of a gene fragment refers to a sequence of nucleotide residues which are at least about 20 nucleotides, at least about 25 nucleotides, at least about 30 nucleotides, at least about 40 nucleotides, at least about 50 nucleotides, or at least about 100 nucleotides. The fragment is typically less than about 400 nucleotides, less than about 300 nucleotides, less than about 250 nucleotides, less than about 200 nucleotides, or less than 150 nucleotides. In certain embodiments, the fragments can be used in various hybridization procedures or microarray procedures to identify specific pathogens.

By "isolated", when referring to a nucleic acid (e.g., an oligonucleotide) is meant a nucleic acid that is apart from a substantial portion of the genome in which it naturally occurs. For example, any nucleic acid that has been produced synthetically (e.g., by serial base condensation) is considered to be isolated. Likewise, nucleic acids that are recombinantly expressed, produced by a primer extension reaction (e.g., PCR), or otherwise excised from a genome are also considered to be isolated.

The term "multiplex primer extension reaction" as used herein refers to a primer extension reaction that is capable of simultaneously producing complementary copies of two or more target nucleic acids within the same reaction vessel. Each reaction product is primed using a distinct primer pair. A multiplex reaction may further include specific probes for each product that are detectably labeled with different detectable moieties. In preferred embodiments, the multiplex primer extension reaction is a multiplex PCR in which two or more products within the same reaction vessel are amplified.

As used herein, the term "oligonucleotide" refers to a short polymer composed of deoxyribonucleotides, ribonucleotides or any combination thereof. Oligonucleotides are generally between about 10, 11, 12, 13, 14 or 15 to about 150 nucleotides (nt) in length, more preferably about 10, 11, 12, 13, 14, or 15 to about 70 nt, and most preferably between about 18 to about 26 nt in length. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymidine (uracil if RNA); and "M" means adenine or cytosine. An oligonucleotide may be used as a primer or as a probe.

Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

By "pathogen" is meant any microbial organism capable of causing whooping cough or a related condition in a mammal (e.g., a human). Specific pathogens include, for example, *Bordetella pertussis* and *Borderella parapertussis*.

As used herein, a "primer" for amplification is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal expression and amplification. The term "primer" as used herein includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of dsDNA. A "reverse primer" is complementary to the sense-strand of dsDNA. A "primer pair" refers to the combination of a forward primer and a reverse primer, each specific for the same target nucleic acid.

Primers are typically between about 10 and about 100 nucleotides in length, preferably between about 10 and about 60 nucleotides in length, and most preferably between about 13 and about 25 nucleotides in length (e.g., 13, 15, 17, 19, 21, or 23 nucleotides in length). There is no standard length for optimal hybridization or polymerase chain reaction amplification. An optimal length for a particular primer application may be readily determined in the manner described in H. Erlich, PCR Technology, Principles and Application for DNA Amplification, (1989).

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions.

By "primer extension reaction" is meant a synthetic reaction in which an oligonucleotide primer hybridizes to a target nucleic acid and a complementary copy of the target nucleic acid is produced by the polymerase-dependent 3'-addition of individual complementary nucleotides. In preferred embodiments, the primer extension reaction is PCR.

As used herein, the term "sample" or "biological sample" refers to clinical samples obtained from a patient (e.g., a human patient). In preferred embodiments, a sample is obtained from tissue, bodily fluid, or microorganisms collected from a subject. Sample sources include, but are not limited to, mucus, sputum (processed or unprocessed), bronchial alveolar lavage (BAL), bronchial wash (BW), blood (e.g., whole blood, plasma, and serum), bodily fluids, cerebrospinal fluid (CSF), urine, plasma, scrum, or tissue (e.g., biopsy material). Preferred sample sources include nasopharyngeal and/or throat swabs.

As used herein, "Scorpion primer" refers to an oligonucleotide comprising a 3' primer with a 5' extended probe tail comprising a hairpin structure which possesses a fluorophore/quencher pair. Optionally, the Scorpion primer further contains an amplification blocker (e.g., hexethylene glycol ("HEG") separating the probe moiety from the primer moiety. As described in more detail herein, the Scorpion™ primers are examples of Scorpion primers.

As used herein, the term "Scorpion™ detection system" refers to a method for real-time PCR. This method utilizes a bi-functional molecule (referred to herein as a "Scorpion™"), which contains a PCR primer element covalently linked by a polymerase-blocking group to a probe element. Additionally, each Scorpion™ molecule contains a fluorophore that interacts with a quencher to reduce the background fluorescence.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art. As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

As used herein, the term "substantially identical", when referring to a nucleic acid, is one that has at least 80%, 85%, 90%, 95%, or 99% sequence identify to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

By "suitable for amplifying," when referring to oligonucleotide primer or primer pairs, is meant primers that specifically hybridize to a target nucleic acid and are capable of providing an initiation site for a primer extension reaction in which a complementary copy of the target nucleic acid is synthesized.

The terms "target nucleic acid" or "target sequence" as used herein refer to a sequence which includes a segment of nucleotides of interest to be amplified and detected. Copies of the target sequence which are generated during the amplification reaction are referred to as amplification products, amplimers, or amplicons. Target nucleic acid may be composed of segments of a chromosome, a complete gene with or without intergenic sequence, segments or portions of a gene with or without intergenic sequence, or sequence of nucleic acids which probes or primers are designed. Target nucleic acids may include a wild-type sequence(s), a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be DNA or RNA extracted from a cell or a nucleic acid copied or amplified therefrom, or may include extracted nucleic acids further converted using a bisulfite reaction.

As used herein "TaqMan® PCR detection system" refers to a method for real time PCR. In this method, a TaqMan® probe which hybridizes to the nucleic acid segment amplified is included in the PCR reaction mix. The TaqMan®, probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

Biological Sample Collection and Preparation

The methods and compositions of this invention may be used to detect pathogens that cause whooping cough by detecting pathogen nucleic acids in a biological sample obtained from an individual. Samples for pathogen detection may also comprise cultures of isolated bacteria grown on appropriate media to form colonies, wherein the cultures were prepared from a biological sample obtained from an individual.

The nucleic acid (DNA or RNA) may be isolated from the sample according to any methods well known to those of skill in the art. If necessary the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of DNA derived from the pathogens, if present in the sample, to detect using polymerase chain reaction.

Various methods of DNA extraction are suitable for isolating the DNA. Suitable methods include phenol and chloroform extraction. See Maniatis et al., Molecular Cloning, A Laboratory Manual, 2d, Cold Spring Harbor Laboratory Press, page 16.54 (1989). Numerous commercial kits also yield suitable DNA including, but not limited to, QIAamp™ mini blood kit, Agencourt Genfind™, Roche Cobas® Roche MagNA Pure® or phenol:chloroform extraction using Eppendorf Phase Lock Gels®.

Target Nucleic Acids and Primers

In various embodiments of the present invention, oligonucleotide primers and probes are used in the methods described herein to amplify and detect target sequences of pathogens. In certain embodiments, target nucleic acids may include the IS481 insertion sequence (and fragments thereof) from *B. pertussis*, and the IS1001 insertion sequence (and fragments thereof) from *B. parapertussis*. In addition, primers can also be used to amplify one or more control nucleic acid sequences. The target nucleic acids described herein may be detected singly or in a multiplex format, utilizing individual labels for each target.

The skilled artisan is capable of designing and preparing primers that are appropriate for amplifying a target sequence in view of this disclosure. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill in the art.

Primers that amplify a nucleic acid molecule can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis or real-time PCR), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 35 nucleotides in length.

Designing oligonucleotides to be used as hybridization probes can be performed in a manner similar to the design of primers. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 60 nucleotides in length.

In some embodiments, a mix of primers is provided having degeneracy at one or more nucleotide positions. Degenerate primers are used in PCR where variability exists in the target sequence, i.e. the sequence information is ambiguous. Typically, degenerate primers will exhibit variability at no more than about 4, no more than about 3, preferably no more than about 2, and most preferably, no more than about 1 nucleotide position.

In a suitable embodiment, PCR is performed using a bifunctional primer/probe combination (e.g., Scorpion™ primers). Scorpion primers, as used in the present invention comprise a 3' primer with a 5' extended probe tail comprising a hairpin structure which possesses a fluorophore/quencher pair. During PCR, the polymerase is blocked from extending into the probe tail by the inclusion of hexethlyene glycol (HEG). During the first round of amplification the 3' target-specific primer anneals to the target and is extended such that the Scorpion™ is now incorporated into the newly synthesized strand, which possesses a newly synthesized target region for the 5' probe. During the next round of denaturation and annealing, the probe region of the Scorpion primer hairpin loop will hybridize to the target, thus separating the fluorophore and quencher and creating a measurable signal. Such probes are described in Whitcombe et al., Nature Biotech 17: 804-807 (1999).

Amplification of Nucleic Acids

Nucleic acid samples or isolated nucleic acids may be amplified by various methods known to the skilled artisan. Preferably, PCR is used to amplify nucleic acids of interest. Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase. When the template is sequence-modified, as described above, the amplification mixture preferably does not contain a UNG nuclease.

If the target sequence is present in a sample, the primers will bind to the sequence and the polymerase will cause the primers to be extended along the target sequence by adding on nucleotides. By raising and lowering the temperature of the reaction mixture, the extended primers will dissociate from the marker to form reaction products, excess primers will bind to the marker and to the reaction products and the process is repeated, thereby generating amplification products. Cycling parameters can be varied, depending on the length of the amplification products to be extended. An internal positive amplification control (IPC) can be included in the sample, utilizing oligonucleotide primers and/or probes. The IPC can be used to monitor both the conversion process and any subsequent amplification.

In a suitable embodiment, real time PCR is performed using any suitable instrument capable of detecting the accumulation of the PCR amplification product. Most commonly, the instrument is capable of detecting fluorescence from one or more fluorescent labels. For example, real time detection on the instrument (e.g. an ABI Real-Time PCR System 7500® sequence detector) monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually.

Detection of Amplified Target Nucleic Acids

Amplification of nucleic acids can be detected by any of a number of methods well-known in the art such as gel electrophoresis, column chromatography, hybridization with a probe, sequencing, melting curve analysis, or "real-time" detection.

In the preferred approach, sequences from two or more fragments of interest are amplified in the same reaction vessel (i.e. "multiplex PCR"). Detection can take place by measuring the end-point of the reaction or in "real time." For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the TaqMan® system, Scorpion™ primer system and use of intercalating dyes for double stranded nucleic acid.

In end-point detection, the amplicon(s) could be detected by first size-separating the amplicons, then detecting the size-separated amplicons. The separation of amplicons of different sizes can be accomplished by, for example, gel electrophoresis, column chromatography, or capillary electrophoresis. These and other separation methods are well-known in the art. In one example, amplicons of about 10 to about 150 base pairs whose sizes differ by 10 or more base pairs can be separated, for example, on a 4% to 5% agarose gel (a 2% to 3% agarose gel for about 150 to about 300 base pair amplicons), or a 6% to 11% polyacrylamide gel. The separated nucleic acids can then be stained with a dye such as ethidium bromide and the size of the resulting stained band or bands can be compared to a standard DNA ladder.

In some embodiments, amplified nucleic acids are detected by hybridization with a specific probe. Probe oligonucleotides, complementary to a portion of the amplified target sequence may be used to detect amplified fragments. Hybridization may be detected in real time or in non-real time. Amplified nucleic acids for each of the target sequences may be detected simultaneously (i.e., in the same reaction vessel) or individually (i.e., in separate reaction vessels). In preferred embodiments, the amplified DNA is detected simultaneously, using two or more distinguishably-labeled, gene-specific oligonucleotide probes, one which hybridizes to the first target sequence and one which hybridizes to the second target sequence. For sequence-modified nucleic acids, the target may be independently selected from the top strand or the bottom strand. Thus, all targets to be detected may comprise top strand, bottom strand, or a combination of top strand and bottom strand targets.

The probe may be detectably labeled by methods known in the art. Useful labels include, for example, fluorescent dyes (e.g., Cy5®, Cy3®, FITC, rhodamine, lanthamide phosphors, Texas red, FAM, JOE, Cal Fluor Red 610®, Quasar 670®, radioisotopes (e.g., $^{32}P$, $^{35}S$, $^{3}H$, $^{14}C$, $^{125}I$, $^{131}I$), electron-dense reagents (e.g., gold), enzymes (e.g., horseradish peroxidase, beta-galactosidase, luciferase, alkaline phosphatase), calorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

One general method for real time PCR uses fluorescent probes such as the TaqMan®; probes, molecular beacons, and Scorpions. Real-time PCR quantifies the initial amount of the template with more specificity, sensitivity and reproducibility, than other forms of quantitative PCR, which detect the amount of final amplified product. Real-time PCR does not detect the size of the amplicon. The probes employed in Scorpion™ and TaqMan® technologies are based on the principle of fluorescence quenching and involve a donor fluorophore and a quenching moiety.

In a preferred embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion™ type probes.

Suitable fluorescent moieties include the following fluorophores known in the art: 4-acetamido-4'-isothiocyanatostilbene-2,2'disulfonic acid, acridine and derivatives (acridine, acridine isothiocyanate) Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, BODIPY® R-6G, BOPIPY® 530/550, BODIPY® FL, Brilliant Yellow, coumarin and derivatives (coumarin, 7-amino-4-methylcoumarin (AMC, Coumarin 120), 7-amino-4-trifluoromethylcouluarin (Coumarin 151)), Cy2®, Cy3®, Cy3.5®, Cy5®, Cy5.5®, cyanosine, 4',6-diaminidino-2-phenylindole (DAPI), 5',5''-dibromopyrogallol-sulfonephthalein (Bromopyrogallol Red), 7-diethyl amino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenyl azo)benzoic acid (DAB CYL), 4-dimethylaminophenylazophenyl-4'-isothiocyanate (DABITC), Eclipse™ (Epoch Biosciences Inc.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl) aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET)), fluorescamine, IR144, IR1446, Malachite Green isothiocyanate, 4-methylumbelliferone, ortho cresolphthalein, nitrotyrosine, pararosaniline, Phenol Red, B-phycoerythrin, R-phycoerythrin, o-phthaldialdehyde, Oregon Green®, propidium iodide, pyrene and derivatives (pyrene, pyrene butyrate, succinimidyl 1-pyrene butyrate), QSY® 7, QSY® 9, QSY® 21, QSY® 935 (Molecular Probes), Reactive Red 4 (Cibacron® Brilliant Red 3B-A), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red)), N,N,N',N'-tetramethyl-6-carboxyrhodamine (TAMRA), tetramethyl rhodamine, tetramethyl rhodamine isothiocyanate (TRITC), riboflavin, rosolic acid, terbium chelate derivatives.

Other fluorescent nucleotide analogs can be used, see, e.g., Jameson, 278 Meth. Enzymol. 363-390 (1997); Zhu, 22 Nucl. Acids Res. 3418-3422 (1994). U.S. Pat. Nos. 5,652, 099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135, 717 describes phthalocyanine and tetrabenztriazaporphyrin reagents for use as fluorescent labels.

Suitable quenchers are selected based on the fluorescence spectrum of the particular fluorophore. Useful quenchers include, for example, the Black Hole™ quenchers BHQ-1, BHQ-2, and BHQ-3 (Biosearch Technologies, Inc.), and the ATTO-series of quenchers (ATTO 540Q, ATTO 580Q, and ATTO 612Q; Atto-Tec GmbH).

The detectable label can be incorporated into, associated with or conjugated to a nucleic acid. Label can be attached by spacer arms of various lengths to reduce potential steric hindrance or impact on other useful or desired properties. See, e.g., Mansfield, 9 Mol. Cell. Probes 145-156 (1995). Detectable labels can be incorporated into nucleic acids by covalent or non-covalent means, e.g., by transcription, such as by random-primer labeling using Klenow polymerase, or nick translation, or amplification, or equivalent as is known in the art. For example, a nucleotide base is conjugated to a detectable moiety, such as a fluorescent dye, and then incorporated into nucleic acids during nucleic acid synthesis or amplification.

With Scorpion primers, sequence-specific priming and PCR product detection is achieved using a single molecule. The Scorpion primer maintains a stem-loop configuration in the unhybridized state. The fluorophore is attached to the 5' end and is quenched by a moiety coupled to the 3' end, although in suitable embodiments, this arrangement may be switched. The 3' portion of the stem and/or loop also contains sequence that is complementary to the extension product of the primer. This sequence is linked to the 5' end of a specific primer via a non-amplifiable monomer. After extension of the primer moiety, the specific probe sequence is able to bind to its complement within the extended amplicon thus opening up the hairpin loop. This prevents the fluorescence from being quenched and a signal is observed. A specific target is amplified by the reverse primer and the primer portion of the Scorpion primer, resulting in an extension product. A fluorescent signal is generated due to the separation of the fluorophore from the quencher resulting from the binding of the probe element of the Scorpion primer to the extension product.

TaqMan® probes (Heid, et al., Genome Res 6: 986-994, 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). Sec Tyagi, et al., 16 Nature Biotechnology 49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

Detection of *Bordetella pertussis*

The presence of *B. pertussis* in a patient may be determined by detecting the presence of a nucleic acid encoding IS481 insertion sequence, or a diagnostic fragment thereof, in a biological sample. The nucleotide sequence of *B. pertussis* IS481 is provided at Genbank Accession No. M28220 and is shown in FIG. 1 (SEQ ID NO: 1).

In preferred embodiments, the target nucleic acid corresponds to nucleotides 553-693 of IS481 or a fragment thereof, and is provided below as SEQ ID NO: 2.

```
                                                    SEQ ID NO: 2
  1 gcgccctggc caccgggtca cgggcaaccg acgcgatacc gttgaggggg ccggctggga 61 cttcgtcttc gtggccatcg atgaccacgc ccgcgtggcc ttcaccgaca tcccccccga 121 cgagcgcttc cccagcgccg t
```

The full target nucleic acid sequence, or any portion thereof, may be amplified and detected using any appropriate primers and probes. One particularly useful target nucleic acid sequence encompasses nucleotides 580-665 of IS481 (SEQ ID NO: 3), corresponding to nucleotides 28-113 of SEQ ID NO: 2. Useful primers include, for example, those directed to nucleotides 580-597 (SEQ ID NO: 4) and 648-665 (SEQ ID NO: 5) of IS481, or complements thereof (underlined in the target nucleic acid provided above). Useful probes are directed to any useful region of the amplified IS481 sequence. Useful probes include, for example, nucleotides 623-642 (SEQ ID NO: 6) and nucleotides 604-628 (SEQ ID NO: 27) of IS481, or a complement thereof, which correspond to nucleotides 71-90 and 52-76 of SEQ ID NO: 2, respectively.

A BLAST search with the probe of SEQ ID NO: 6 reveals a complete match with the IS481 target nucleic acid sequence of *B. pertussis* and *B. holmesii*. Additionally, there is an 18/20 nucleotide match within *Pseudomonas fluoroescens* genome, and a 17/20 nucleotide match within the *Magnaporthe grisea* and the *Xanthomonas oryzae* genomes. As noted below, there is no significant sequence identity for *P. fluorescens*, *M. grisea*, and *X. oryzae* with the primers of SEQ ID NOs: 4-5. Accordingly, these species should not be a significant source of false positives when amplification primers of SEQ ID NOs: 4-5 are used. Cross-reactivity of the probe of SEQ ID NO: 6 may be reduced or eliminated using high stringency hybridization conditions sufficient to inhibit hybridization at this level of non-homology.

A BLAST search with the primer sequences of SEQ ID NOs: 4-5 show complete homology with the IS481 target nucleic acid sequence of *B. pertussis* and *B. holmesii*. Human infection by *B. holmesii* is rare, but may be detected using the primers and probes described herein. Also found were 15-17 nucleotide matches with sequences in the *Bordetella avium*, *Methylobacillus flagellatus*, *Rhodococcus*, and *Rubrobacter xylanophilus* genomes. However, these bacteria and fungi are not known to infect humans so should not be a significant cause of false positive diagnostic results.

Detection of *Bordetella parapertussis*

The presence of *B. parapertussis* in a patient may be determined by detecting the presence of a nucleic acid encoding IS1001 insertion sequence, or a diagnostic fragment thereof, in a biological sample. The nucleotide sequence of *B. parapertussis* IS 1001 is provided at Genbank Accession No. X66858 and is shown in FIG. 2 (SEQ ID NO: 7). In preferred embodiments, the target nucleic acid corresponds to nucleotides 680-859 of IS1001 or a fragment thereof, and is provided below as SEQ ID NO: 8.

```
                                                    SEQ ID NO: 8
  1 caattgccgc ctggggccgc ccaacgcatc aaggccgttg ccatcgacat gaccaccgcc 61 tacgagttGG AGATCCAGGC CCacagccca caggcggaga tcgtctatga cttgttccat 121 gtcgtggcca agtatggacg agaggtcatt gatcgggtgc gcgtggatca ggccaatcaa
```

The full target nucleic acid sequence, or any portion thereof, may be amplified and detected using any appropriate primers and probes. One particularly useful target nucleic acid sequence encompasses nucleotides 730-802 of IS1001 (SEQ ID NO: 9), corresponding to nucleotides 51-123 of SEQ ID NO: 8. Useful primers include, for example, those directed to nucleotides 730-747 (SEQ ID NO: 10) and 777-802 (SEQ ID NO: 11) of IS1001, or complements thereof (underlined in the target nucleic acid provided above). One useful probe is directed to nucleotides 748-761 (SEQ ID NO: 12) of IS1001, or a complement thereof (capitalized in the target nucleic acid provided above).

A BLAST search with the primers of SEQ ID NOs: 10-11 reveal complete matches with the IS1001 target nucleic acid sequence of *B. parapertussis*. Additionally, the primer of SEQ ID NO: 10 shows 16-, and 17-nucleotide matches within the genomes of *Acanthostigma perpusillum*, *Rhodobacter sphaeroides*, *Bradyrhizobium japonicum*, and *Satinibacter ruber*. The primer of SEQ ID NO: 11 shows only short and insignificant matches with any relevant species.

EXAMPLES

Example 1: Sample Collection and DNA Extraction

A total of 306 nasopharyngeal swab samples were prepared and tested for assay validation purposes. Of the 306 samples, 290 were actual clinical specimens obtained from patients. The remaining 16 samples were "contrived" (i.e., positive control) *B. parapertussis* specimens. The contrived specimens were prepared by spiking pathogen-negative nasopharyngeal swab matrix with cultured *B. parapertussis* organisms.

The nasopharyngeal swabs were collected from patients and placed immediately in Aimes media with charcoal or in liquid viral transport media (Micro Test™ M4 media; Remel, Inc.), frozen at −20° C. for transport, and stored at −20° C. until assayed.

For the *Bordetella* spp. assays described below, DNA was extracted from the nasopharyngeal swab samples. Briefly, the samples were thawed and 200 µl of each sample was aliquoted into 1.5 ml Eppendorf tubes. Additional tubes containing 200 Pl of diluent with positive control DNA (see below) or no DNA (negative control) were prepared and processed simultaneously with the patient samples. 5 µl of internal control DNA (see below) was then added to each sample. The QIAamp™ mini blood kit (Qiagen) was used to extract the DNA according to the manufacturer's instructions.

The internal control (IC) DNA consists of a DNA fragment of random sequence not present in any of the assayed organisms. Two oligonucleotides with 5' phosphate (pIC F 5'P and pIC R 5'p) were annealed, and the product was cloned into EcoRI site of pUC19.

```
(pIC F 5'P):
                                        (SEQ ID NO: 15)
5' Phosphate-aaTTCGCCCT TTGTTTCGAC CTAGCTTGCC
AGTTCGCAGAA TTTGTTGCTC GTCAGTCGTC GGCGGTTTTA
agggcg (pIC R 5'P)
                                        (SEQ ID NO: 16)
5' Phosphate-aattcgccct TAAAACCGCC GACGACTGAC
GAGCAACAAA TTCTGCGAAC TGGCAAGCTA GGTCGAAACA
AAGGGCG
```

The IC amplicon was generated by the following primers which anneals to the pUC19 sequences.

```
                                        (SEQ ID NO: 17)
Forward primer (PUC-For):    5' GTTTTCCCAG TCACGACGTT GTA (SEQ ID NO: 18)
Reverse primer (PUC-Rev):    5' CACTTTATGC TTCCGGCTCG TA Sequence of IC amplicon:
                                        (SEQ ID NO: 19)
  1 GTTTTCCCAG TCACGACGTT GTAAAACGAC GGCCAGTGAA TTCgcccttt aaaccgccga 81 cgactgacga gcaacaaatt ctgcgaactg gcaagctagg tcgaaacaaa gggcggattc

121 GAGCTCGGTA CCCGGGGATC CTCTAGAGTC GACCTGCACG CATGCAAGCT TGGCGTAATC

181 ATCCTCATAG CTGTTTCCTG TGTGAAATTG TTATCCGCTC ACAATTCCAC ACAACATACG

241 AGCCGGAAGC ATAAAGTG
```

Underlined sequences are part of Multiple Cloning Site (MCS) of pUC19. Lowercase sequences were generated by annealing two complementary oligonucleotides. IC amplicon was generated by the following primers which anneals to the pUC19 sequences.

For all assays, positive and negative controls were prepared and run simultaneously with the patient samples. The positive control DNA consisted of a 625 bp DNA fragment containing IS481 and S11001 target regions of *B. pertussis* and *A. parapertussis*, respectively, in a single molecule. Negative control assays contained no DNA.

To construct the positive control template, primers were designed to amplify the target regions of IS481 and IS1001, and clone them in tandem into the pUC19 plasmid. The IS481 forward primer was designed with an EcoRI restriction site added (IS481 EcoRI F) while the IS481 reverse primer was designed with a BamHI restriction site added (IS481 BamHI R). These primers were then used to generate a 237 bp amplicon from IS481 of *B. pertussis*.

```
IS481 EcoRI F:
                                        (SEQ ID NO: 20)
5' agcagtgaat tcggtggtgc gctacgagca IS481 BamHI R:
                                        (SEQ ID NO: 21)
5' atatgcggat ccgccactgc gtccttgagga
```

The IS1001 forward primer was designed with a BamHI restriction site added (IS1001 BamHI F) and the IS1001 reverse primer was designed with a PstI restriction site added (IS1001 PstI R).

```
IS1001 BamHI F:
                                        (SEQ ID NO: 22)
5' atatgcggat ccataccgtc aagacgctgg aca IS1001 PstI R:
                                        (SEQ ID NO: 23)
5' tagcaactgc agcgatcaat gacctctcgt ccata
```

These primers were used to generate a 358 bp amplicon from IS1001 of *B. parapertaissis*.

The amplicons were then purified and ligated simultaneously into pUC19 plasmid previously digested with EcoRI and PstI using T4 DNA ligase. The ligated plasmids were transformed into *E. coli* followed by selective growth on LB agar containing ampicillin. Single colonies were selected and DNA was prepared. This DNA was used as template DNA in screening by SYBR green real-time PCR using the IS481 forward primer together with the IS1001 reverse primer. Plasmids producing positive SYBR green PCR results were then sequenced to confirm the presence of a 601 bp insert containing a tandemly arranged IS481 and IS1001 targets (595 bp), and the BAMHI restriction site (6 bp).

The positive control amplicon was generated by amplification using the plasmid containing the tandem 601 bp IS481/IS1001 insert as template together with the IS481 EcoRI F and IS1001 PstI R primers. Including the added restriction sites, the total size of the positive control amplicon is 625 hp having the following nucleotide sequence:

```
                                                                    (SEQ ID NO: 24)
  1 agcagtgaat tcggtggtgc gctacgagca tcaggccccc ggcgatctgc tgcacatcga 61 catcaagaag ctgggacgta tccagcgccc tggccaccgg gtcacgggca accgacgcga 121 taccgttgag ggggccggct gggacttcgt cttcgtggcc atcgatgacc acgcccgcgt 181 ggccttcacc gacatccccc ccgacgagcg cttccccagc gccgtccagt tcctcaagga 241 cgcagtggcg gatccatacc gtcaagacgc tggacaaggc tcggctgcgt gcgtcggtgc 301 gcgaaccgga ttggtccaag atcgagtatt tggcgatgga cgagtttgcc ctgcacaaag 361 ggcatcgcta cgcgacagtg gtggtcgatc cgatcggcag gcaggtgctg tggattggcc 421 caggacgctc acgcgagacg gcccgggcgt tcttcgaaca attgccgcct ggggccgccc 481 aacgcatcaa ggccgttgcc atcgacatga ceacegecta cgagttggag atccaggccc 541 acagcccaca ggcggagatc gtctatgact tgttccatgt cgtggccaag tatggacgag 601 aggtcattga tcgctgcagt tgcta
```

Example 2: Multiplex PCR Detection of *Bordetella* spp

The final PCR Reagent Solution contained the following: Tris-HCl (pH 9.0), MgCl$_2$, KCl, EDTA, DTT, Tween 20, (NH$_4$)$_2$SO$_4$, glycerol, d TPs (dT, dA, dG, and dC), and FastStart DNA Polymerase™.

A 10×PCR primer solution was prepared containing Scorpion primers and reverse primers for *B. pertussis*, *B. parapertussis*, and the internal control. The *B. pertussis* Scorpion and reverse primers were at a final concentration of 2 µM, the *B. parapertussis* Scorpion and reverse primers were at a final concentration of 1.5 µM and the IC Scorpion and reverse primers were at a final concentration of 1 µM in the 10×PCR Primer Solution. Two different *B. pertussis* Scorpion primers were individually tested. The primer pairs were as follows:

*B. pertussis* (IS481):
[Q]-GCGTGGTCATCGATGGCCACcacgct-[F]-tttttt-heg-ccgacgcgataccgttga (SEQ ID NOS: 13, 29, and 30, respectively, in order of appearance) and
[Q]-agcGGCCACGAAGACGAAGTCCCAGCCGct-[F]-heg-ccgacgcgataccgttga (SEQ ID NOS: 28 and 30, respectively, in order of appearance); and Reverse Primer: ggatgtcggtgaaggcca (SEQ ID NO: 25).

*B. parapertussis* (IS1001):
[Q]-accGGGCCTGGATCTCCcggt-[F]-heg-gaccaccgcctac-gagtt (SEQ ID NOS: 14 and 31, respectively, in order of appearance), and Reverse Primer: gacatggaacaagtcatagac-gatct (SEQ ID NO: 26).

Internal Contol:
[Q]-TGCGAACTGCCAAGCT-[F]-heg-attcgcccttttgtttcgac-cta (SEQ ID NOS: 32 and 33, respectively, in order of appearance), and
Reverse Primer: CCGACGACTGACGAGCAA (SEQ ID NO: 34).

For each Scorpion primer listed above, Q=quencher, F=fluorophore, and "heg"=hexethylene glycol. The probe sequence is identified by capital letters.

| Scorpion Primer | F | Excitation | Emission | Target Gene |
|---|---|---|---|---|
| *B. pertussis* | FAM | 495 nm | 520 nm | IS481 |
| *B. parapertussis* | CalFlour Red 610 | 590 nm | 610 nm | IS1001 |
| Internal Control | Quasar 670 | 649 nm | 670 nm | See above |

The PCR Reaction Solution was created by mixing 12.5 µl of PCR Reagent Solution, 2.5 µl 10×PCR Primer Solution, and 5 µl of nuclease-free water per sample assay to be performed.

Multiplex PCR detection assays were performed in 96-well plates. Each assay contained 20 µl of the PCR Reaction Solution and 5 µl of extracted nucleic acid (i.e., patient sample, positive control, or negative control). The plates were sealed, centrifuged at 2000×g for 2 minutes, and run in an Applied Biosystems (ABI) 7500 Real-Time PCR Detection System. The PCR reaction was performed as follows:

| Stage 1 (one cycle): | 10 minutes at 95° C. |
|---|---|
| Stage 2 (45 cycles): | Step 1: 95° C. for 15 sec |
| | Step 2: 60° C. for 35 sec |
| | (data collection during Step 2). |

The data was collected and patient samples analyzed for the presence of one or more pathogenic species. Patient samples having a positive result for any one or more of the pathogenic species were scored as positive for those species. Patient samples having a negative result for all pathogenic species were only scored as negative provided that the internal control target nucleic acid was detected and the positive control sample assay was positive for both the *B. pertussis* and *B. parapertussis* target nucleic acids.

Example 3: Confirmation of Multiplex PCR Assay Results

The results of the multiplex assay described above were compared to other detection assays. Aliquots of all samples were run in a secondary assay for confirmation of the multiplex assay result. *B. pertussis* was assessed in the ProPertussis assay (Prodesse, Inc.) which detected a different target nucleic acid within the IS481 insertion sequence as well as a separate internal control. *B. parapertussis* was assessed using a Taqman®-style assay for the IS1001 insertion sequence using primers and probes identical to the primer and probe regions of the Scorpion and reverse primer described above.

Each of the 306 samples was assayed simultaneously for *B. pertussis* and *B. parapertussis* in the multiplex assay. Additionally, the 306 samples were assayed once using the ProPertussis assay, and once using the *B. parapertussis* Taqman® assay. For the *B. pertussis* assays (multiplex and ProPertussis), a Ct value of ≤37.0 was scored as positive. For the *B. parapertussis* assays (multiplex and Taqman®), a Ct value of ≤36.5 was scored as positive. The multiplex assay for three samples failed in the first repetition and two samples failed in repeat testing, most likely due to inhibitory substances in the clinical specimen causing a failure of the internal control. This increased the total from 303 to 304 between Repetition #1 and #2 shown below. Additionally, all the samples that were in disagreement between the two tests for *B. pertussis* or for *B. parapertussis* were repeated with both the multiplex test and the comparator. Results from Repetition #2 include the sample results following any repeat testing. The results of each assay were as follows:

*B. pertussis*:

|  |  | Multiplex Assay Results (Repetition #1) | | |
|---|---|---|---|---|
|  |  | Positive | Negative | Total |
| ProPertussis Assay | Positive | 70 | 3 | 73 |
|  | Negative | 8 | 222 | 230 |
| Results (Repetition #1) | Total | 78 | 225 | 303 |

Sensitivity = 95.9%; Specificity = 96.5%; Concordance = 96.4%

The *B. pertussis* component of the multiplex assay had a 95.9% positive agreement and 96.4% negative agreement with the ProPertussis assay.

|  |  | Multiplex Assay Results (Repetition #2) | | |
|---|---|---|---|---|
|  |  | Positive | Negative | Total |
| ProPertussis Assay | Positive | 75 | 3 | 78 |
|  | Negative | 1 | 225 | 226 |
| Results (Repetition #2) | Total | 76 | 228 | 304 |

Sensitivity = 96.2%; Specificity = 99.6%; Concordance = 98.7%

The *B. pertussis* component of the multiplex assay had a 96.2% positive agreement and 99.6% negative agreement with the ProPertussis assay.

*B. parapertussis*:

|  |  | Multiplex Assay Results (Repetition #1) | | |
|---|---|---|---|---|
|  |  | Positive | Negative | Total |
| Taqman® Assay | Positive | 42 | 4 | 46 |
|  | Negative | 2 | 255 | 257 |
| Results (Repetition #1) | Total | 44 | 259 | 303 |

Sensitivity = 91.3%; Specificity = 99.2%; Concordance = 98.0%

|  |  | Multiplex Assay Results (Repetition #2) | | |
|---|---|---|---|---|
|  |  | Positive | Negative | Total |
| Taqman® Assay | Positive | 44 | 1 | 45 |
|  | Negative | 0 | 259 | 259 |
| Results (Repetition #2) | Total | 44 | 260 | 304 |

Sensitivity = 97.8%; Specificity = 100%; Concordance = 99.7%

The *B. parapertussis* component of the multiplex assay had a 97.8% positive agreement and 100% negative agreement with the Taqman® assay.

Example 4: Cross-Reactivity of the *Bordetella* Multiplex Assay

For cross-reactivity assays, control nasal swab specimens were spiked with one of the test organisms (n=5 for each organism) and the DNA was extracted according to the methods described above. The only exception was for *S. aureus* for which clinical nasal swab specimens known to be *S. aureus*-positive were used (i.e., the *S. aureus* sample was genuine, not contrived). The *Bordetella* multiplex assay was performed on each sample. In each case, a Ct value ≤37.0 was interpreted as a positive result for *B. pertussis* cross-reactivity and a Ct value of ≤36.5 was interpreted as a positive result for *B. parapertussis* cross-reactivity.

No cross-reactivity was measured for the following species:

| | |
|---|---|
| *Bacillus cereus* | *Chlamydophila pneumoniae* |
| *Haemophilus influenzae* | *Klebsiella pneumoniae* |
| *Legionella pneumophila* | *Mycoplasma pneumoniae* |
| *Streptococcus pneumoniae* | *Staphylococcus aureus* |
| *Moraxella catarrhalis* | Influenza A |
| Influenza B | RSV B |

Human Random Control DNA

*Haemophilus parainfluenzae* was also tested for cross-reactivity using five individual contrived nasal swab samples. Each of the five samples were run in duplicate. Two of the samples tested mildly positive for *B. pertussis* in both replicates (Ct values of 36.65 and 36.46 respectively). Each of the positive samples also tested positive for *B. pertussis* in the ProPertussis assay. No cross-reactivity with *B. parapertussis* was observed for any of the organisms listed including *H. parainfluenzae*. Despite the mixed positive results, BLAST searching revealed no homology between the multiplex PCR primers for *B. pertussis* and *B. parapertussis* and *H. parainfluenzae*.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including." "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for identifying the presence or absence of *Bordetella pertussis* and *Bordetella parapertussis* in a biological sample, comprising:
   (a) providing a first primer pair suitable for amplifying an IS481 target nucleic acid comprising the nucleotide sequence of SEQ ID NO: 3 or a full complement thereof, amplifying said IS481 target sequence if present in the sample, and detecting the IS481 target sequence by hybridizing it with an oligonucleotide probe, wherein one primer of the first primer pair comprises a 3'-primer element and a 5'-probe tail, wherein said 5'-probe tail comprises a hairpin structure comprising the oligonucleotide probe and a fluorophore/quencher pair; and
   (b) providing a second primer pair suitable for amplifying an IS1001 target nucleic acid comprising the nucleotide sequence of SEQ ID NO: 9 or a full complement thereof, amplifying said IS1001 target sequence if present in the sample, and detecting the IS1001 target sequence by hybridizing with an oligonucleotide probe, wherein one primer of the second primer pair comprises a 3'-primer element, and a 5'-probe tail, wherein said 5'-probe tail comprises a hairpin structure comprising the oligonucleotide probe and a fluorophore/quencher pair, and comprises the sequence of SEQ ID NOS: 14 and 31 in 5'-to-3' orientation,
   wherein the presence of said IS481 target nucleic acid identifies the presence of *B. pertussis*, and the presence of said IS1001 target nucleic acid identifies the presence of *B. parapertussis*.

2. The method of claim 1, wherein one primer of the first primer pair comprises the sequence of SEQ ID NO: 4 or SEQ ID NO: 25.

3. The method of claim 1, wherein one primer of the first primer pair comprises the sequence of (a) SEQ ID NOS: 13, 29, and 30 in 5'-to-3' orientation or (b) SEQ ID NOS: 28 and 30 in 5'-to-3' orientation.

4. The method of claim 1, wherein one primer of the second primer pair comprises the sequence of SEQ ID NO: 26.

5. The method of claim 1, wherein said method comprises real-time PCR.

6. The method of claim 1 wherein said amplifying in step a) and said amplifying in step b) are conducted simultaneously in a single reaction.

7. The method of claim 1, wherein the 5'-probe tail and the 3'-primer element of the first and second primer pairs are connected by an amplification blocker.

8. A method for identifying the presence or absence of *Bordetella pertussis* and *Bordetella parapertussis* in a biological sample, comprising:
   (a) providing a first primer pair suitable for amplifying an IS481 target nucleic acid comprising the nucleotide sequence of SEQ ID NO: 3 or a full complement thereof, amplifying said IS481 target sequence if present in the sample, and detecting the IS481 target sequence by hybridizing it with an oligonucleotide probe, wherein one primer of the first primer pair comprises a 3'-primer element and a 5'-probe tail, wherein said 5'-probe tail comprises a hairpin structure comprising the oligonucleotide probe and a fluorophore/quencher pair, and comprises the sequence of (a) SEQ ID NOS: 13, 29, and 30 in 5'-to-3' orientation or (b) SEQ ID NOS: 28 and 30 in 5'- to -3' orientation; and
   (b) providing a second primer pair suitable for amplifying an IS1001 target nucleic acid comprising the nucleotide sequence of SEQ ID NO: 9 or a full complement thereof, amplifying said IS1001 target sequence if present in the sample, and detecting the IS1001 target sequence by hybridizing with an oligonucleotide probe, wherein one primer of the second primer pair comprises a 3'-primer element and a 5'-probe tail, wherein said 5'-probe tail comprises a hairpin structure comprising the oligonucleotide probe and a fluorophore/quencher pair; and
   wherein the presence of said IS481 target nucleic acid identifies the presence of *B. pertussis*, and the presence of said IS1001 target nucleic acid identifies the presence of *B. parapertussis*.

9. The method of claim 8, wherein said amplifying in step a) and said amplifying in step b) are conducted simultaneously in a single reaction.

10. The method of claim 8, wherein the 5'-probe tail and the 3'-primer element of the first and second primer pairs are connected by an amplification blocker.

11. The method of claim 8, wherein one primer of the first primer pair comprises the sequence of SEQ ID NO: 25.

12. The method of claim 8, wherein one primer of the second primer pair comprises the sequence of SEQ ID NO: 10 or SEQ ID NO: 26.

13. The method of claim 12, wherein one primer of the second primer pair comprises the sequence of SEQ ID NOS: 14 and 31 in 5'-to-3' orientation.

* * * * *

SEQUENCE LISTING

```
<160> NUMBER OF SEQ ID NOS: 34

<210> SEQ ID NO 1
<211> LENGTH: 1073
<212> TYPE: DNA
<213> ORGANISM: Bordetella pertussis

<400> SEQUENCE: 1
gcgaggccgg ctatctgtga agattcaata ggttgtatgc atggttcatc cgaaccggat        60
ttgagaaact ggaaatcgcc gaccccccag ttcactcaag gagcccggcc ggatgaacac       120
ccataagcat gcccgattga ccttcctacg tcgactcgaa atggtccagc aattgatcgc       180
ccatcaagtt tgtgtgcctg aagcggcccg cgcctatggg gtcaccgcgc cgactgtgcg       240
caaatggctg ggccgcttcc tggctcaggg ccaggcgggc ttggccgatg cgtcctcgcg       300
cccgacggtc tcgccccgag cgattgcgcc ggccaaggcg ctggctatcg tggagctgcg       360
ccgcaagcgg ctgacccaag cgcgcatcgc ccaggcgctg ggcgtgtcag ccagcaccgt       420
cagccgcgtc ctggcccgcg ccggtctgtc gcacctggcc gacctggagc cggccgagcc       480
ggtggtgcgc tacgagcatc aggcccccgg cgatctgctg cacatcgaca tcaagaagct       540
gggacgtatc cagcgccctg gccaccgggt cacgggcaac cgacgcgata ccgttgaggg       600
ggccggctgg gacttcgtct tcgtggccat cgatgaccac gcccgcgtgg ccttcaccga       660 catcccccc  gacgagcgct tccccagcgc cgtccagttc ctcaaggacg cagtggccta       720
ctaccagcgc ctgggcgtga ccatccagcg cttgctcacc gacaatggct cggcctttcg       780
cagccgcgcc ttcgccgcgc tgtgccatga gctgggcatc aagcaccgct ttacccgacc       840
ttaccgccca cagaccaatg gcaaggccga acgcttcatc cagtcggcct tgcgtgagtg       900
ggcttacgct cacacctacc agaactccca acaccgagcg gatgccatga aatcctggct       960
acaccactac aactggcatc gaccccacca aggcatcggg cgcgctgtac ccatctccag      1020
actcaacctg gacgaataca acctattgac agttcacagc tatccggacc ggc            1073

<210> SEQ ID NO 2
<211> LENGTH: 141
<212> TYPE: DNA
<213> ORGANISM: Bordetella pertussis

<400> SEQUENCE: 2
gcgccctggc caccgggtca cgggcaaccg acgcgatacc gttgaggggg ccggctggga        60
cttcgtcttc gtggccatcg atgaccacgc ccgcgtggcc ttcaccgaca tccccccga       120 cgagcgcttc cccagcgccg t                                                141
```

<210> SEQ ID NO 3
<211> LENGTH: 86
<212> TYPE: DNA
<213> ORGANISM: Bordetella pertussis

<400> SEQUENCE: 3
ccgacgcgat accgttgagg gggccggctg ggacttcgtc ttcgtggcca tcgatgacca      60
cgcccgcgtg gccttcaccg acatcc                                          86

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 4
ccgacgcgat accgttga                                                   18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 5
tggccttcac cgacatcc                                                   18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 6
gtggccatcg atgaccacgc                                                 20

<210> SEQ ID NO 7
<211> LENGTH: 1306
<212> TYPE: DNA
<213> ORGANISM: Bordetella parapertussis

<400> SEQUENCE: 7
ggttcatcgc gcaataacgt ggagggtttt ggcaattttc gtattcttga cggcaggtat      60
ttgacatcag gagtgcaggg agatgctgga tcgcaagttg atggagtcgc tgggaggctg     120
gcagggctat ggcgtcgaac gcgtggaatg gcccgaagac ccagggcgca cgctgtcgat     180
ctatttgaag ccaacggcca aggtgatgct gtgcgagcag tgcggcgcgc ggtgtcgcca     240
ggtgcatgag accacggttc gacgggtgcg agatctgccg atattcgagt atcgggtcgt     300
tctgcacgtg ccgcgccgac gcttgtggtg tgagcaatgc ggcggcccgc gcctggagcg     360
gcttgcctgg ctggggcgat atcaacgggt gacggatcgg ctggcgcagg cctgcagcca     420
attgctgcaa tcgagcaacg tgcaggcggt ggcgaggttc ttcgaactgg gttggcatac     480
cgtcaagacg ctggacaagg ctcggctgcg tgcgtcggtg cgcgaaccgg attggtccaa     540
gatcgagtat ttggcgatgg acgagtttgc cctgcacaaa gggcatcgct acgcgacagt     600

```
ggtggtcgat ccgatcggca ggcaggtgct gtggattggc ccaggacgct cacgcgagac      660
ggcccgggcg ttcttcgaac aattgccgcc tggggccgcc caacgcatca aggccgttgc      720
catcgacatg accaccgcct acgagttgga gatccaggcc cacagcccac aggcggagat      780
cgtctatgac ttgttccatg tcgtggccaa gtatggacga gaggtcattg atcgggtgcg      840
cgtggatcag gccaatcaac tacgccagga tcgtcccgca cgcaggatca tcaaatcgag      900
tcgctggctg ctgctgcgca accgtgacaa cctggatcgg cagcaggccg tccggctcga      960
cgaattgctg caagccaacc agccgctgct gacggtctat gtcctgcgtg acgaactcaa     1020
acggctctgg ttctaccaaa gacctgcctg ggcaagacaa gcctggaacc actggtacga     1080
gcaggccgag caaagcggaa tagccgcctt gaacaccttc gctcagcgct gaaaggcta      1140 tctgcacggc atcctggcca gatgccgaca tcccctgaac accagcattg tcgagggcat     1200
caacaacact atcaaggtca tcaagcggcg cgcttacggc taccgcgacc aggaatactt     1260
cttcctcaaa atccgtgccg ccttccccgg caatgcgcga tgaacc                    1306
```

<210> SEQ ID NO 8
<211> LENGTH: 180
<212> TYPE: DNA
<213> ORGANISM: Bordetella parapertussis

<400> SEQUENCE: 8

```
caattgccgc ctggggccgc ccaacgcatc aaggccgttg ccatcgacat gaccaccgcc       60
tacgagttgg agatccaggc ccacagccca caggcggaga tcgtctatga cttgttccat      120
gtcgtggcca agtatggacg agaggtcatt gatcgggtgc gcgtggatca ggccaatcaa      180
```

<210> SEQ ID NO 9
<211> LENGTH: 73
<212> TYPE: DNA
<213> ORGANISM: Bordetella parapertussis

<400> SEQUENCE: 9

```
gaccaccgcc tacgagttgg agatccaggc ccacagccca caggcggaga tcgtctatga       60
cttgttccat gtc                                                         73
```

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
gaccaccgcc tacgagtt                                                    18
```

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
agatcgtcta tgacttgttc catgtc                                           26
```

<210> SEQ ID NO 12
<211> LENGTH: 14

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggagatccag gccc                                                           14

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgtggtcat cgatggccac cacgct                                              26

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
accgggcctg gatctcccgg t                                                   21

<210> SEQ ID NO 15
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aattcgccct tgtttcgac ctagcttgcc agttcgcaga atttgttgct cgtcagtcgt          60
cggcggtttt aagggcg                                                        77

<210> SEQ ID NO 16
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aattcgccct taaaaccgcc gacgactgac gagcaacaaa ttctgcgaac tggcaagcta         60
ggtcgaaaca aagggcg                                                        77

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gttttcccag tcacgacgtt gta                                                 23
```

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cactttatgc ttccggctcg ta                                            22

<210> SEQ ID NO 19
<211> LENGTH: 258
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gttttcccag tcacgacgtt gtaaaacgac ggccagtgaa ttcgccctta aaaccgccga    60
cgactgacga gcaacaaatt ctgcgaactg caagctagg tcgaaacaaa gggcggattc   120
gagctcggta cccggggatc ctctagagtc gacctgcagg catgcaagct tggcgtaatc   180
atggtcatag ctgtttcctg tgtgaaattg ttatccgctc acaattccac acaacatacg   240
agccggaagc ataaagtg                                                 258

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agcagtgaat tcggtggtgc gctacgagca                                    30

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atatgcggat ccgccactgc gtccttgagg a                                  31

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atatgcggat ccataccgtc aagacgctgg aca                                33

<210> SEQ ID NO 23
<211> LENGTH: 35
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 23
tagcaactgc agcgatcaat gacctctcgt ccata                                    35

<210> SEQ ID NO 24
<211> LENGTH: 625
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
agcagtgaat cggtggtgc gctacgagca tcaggccccc ggcgatctgc tgcacatcga          60
catcaagaag ctgggacgta tccagcgccc tggccaccgg gtcacgggca accgacgcga       120
taccgttgag ggggccggct gggacttcgt cttcgtggcc atcgatgacc acgcccgcgt       180
ggccttcacc gacatccccc ccgacgagcg cttccccagc gccgtccagt tcctcaagga       240
cgcagtggcg gatccatacc gtcaagacgc tggacaaggc tcggctgcgt gcgtcggtgc       300
gcgaaccgga ttggtccaag atcgagtatt tggcgatgga cgagtttgcc ctgcacaaag       360
ggcatcgcta cgcgacagtg gtggtcgatc cgatcggcag gcaggtgctg tggattggcc       420
caggacgctc acgcgagacg gcccgggcgt tcttcgaaca attgccgcct ggggccgccc       480
aacgcatcaa ggccgttgcc atcgacatga ccaccgccta cgagttggag atccaggccc       540
acagcccaca ggcggagatc gtctatgact tgttccatgt cgtggccaag tatggacgag       600
aggtcattga tcgctgcagt tgcta                                             625

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggatgtcggt gaaggcca                                                      18

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gacatggaac aagtcataga cgatct                                             26

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cggctgggac ttcgtcttcg tggcc                                              25

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agcggccacg aagacgaagt cccagccgct                                    30

<210> SEQ ID NO 29
<211> LENGTH: 6
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29 tttttt                                                               6

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccgacgcgat accgttga                                                 18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gaccaccgcc tacgagtt                                                 18

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgcgaactgg caagct                                                   16

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
attcgccctt tgtttcgacc ta                                            22

```
<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccgacgactg acgagcaa                                                  18
```